Figure 1:
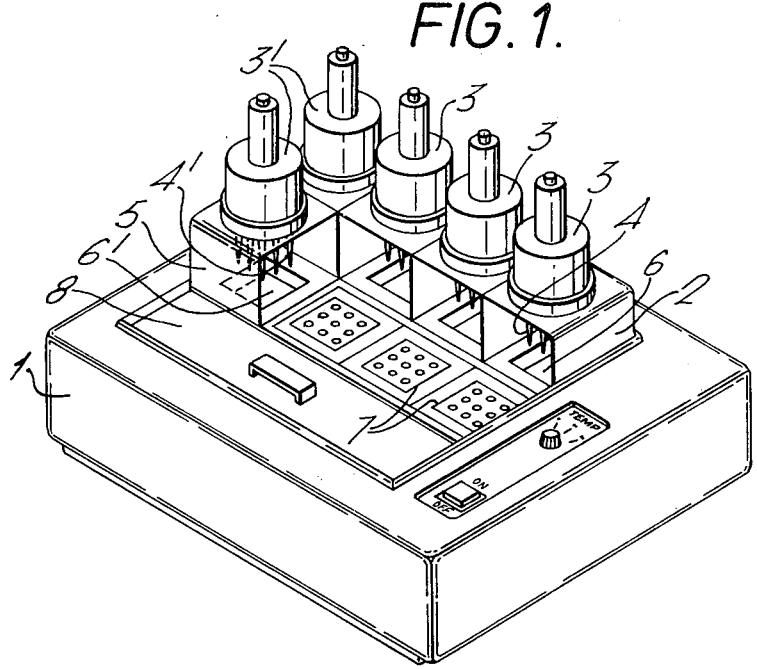

United States Patent [19]

Suovaniemi

[11] 4,058,370

[45] Nov. 15, 1977

[54] APPARATUS FOR ACCURATE PIPETTING OF SMALL LIQUID VOLUMES

[76] Inventor: Osmo Antero Suovaniemi, Armas Lindgrenintie 15 A, 00570 Helsinki 57, Finland

[21] Appl. No.: 544,132

[22] Filed: Jan. 27, 1975

[30] Foreign Application Priority Data

July 5, 1974 Finland ................................. 742083

[51] Int. Cl.$^2$ .......................... B01L 3/02; B01L 9/00; B01L 11/00; C01N 31/00
[52] U.S. Cl. .................................... 23/259; 23/230 R; 73/425.4 P; 195/143
[58] Field of Search ............................ 23/259, 253 R; 73/425.4 P, 425.6 R; 195/143; 206/305

[56] References Cited

U.S. PATENT DOCUMENTS

| | | | |
|---|---|---|---|
| 3,549,330 | 12/1970 | Jungner et al. | 23/259 |
| 3,551,112 | 12/1970 | Sequeira | 23/253 R X |
| 3,622,047 | 11/1971 | Oberli | 23/259 X |
| 3,650,306 | 3/1972 | Lancaster et al. | 23/259 X |
| 3,728,079 | 4/1973 | Moran | 23/259 X |
| 3,790,346 | 2/1974 | Ritchie | 23/259 X |
| 3,852,035 | 12/1974 | Wood et al. | 23/253 R |
| 3,855,868 | 12/1974 | Sudvaniemi | 73/425.6 |

Primary Examiner—Morris O. Wolk
Assistant Examiner—Michael S. Marcus
Attorney, Agent, or Firm—Woodling, Krost, Granger & Rust

[57] ABSTRACT

Apparatus for the accurate pipetting of small liquid volumes for sample and reagent mixtures which include a pipette with a point at least partly fitted in a thermo-regulated space in one single pipetting-incubating station in such a way that at least the liquid container of the pipette is in the thermo-regulated space. Sample reagent or reaction mixture test tubes, and when necessary, also, a shaker and/or a storage section or a container are, also, fitted in the pipetting-incubating station and are thermo-regulated at the same temperature so that the pipetting, shaking and storage of samples and reaction mixtures can be carried out in a centralized manner within one single pipetting-incubating station, in conditions thermo-regulated in an exact predetermined way.

6 Claims, 26 Drawing Figures

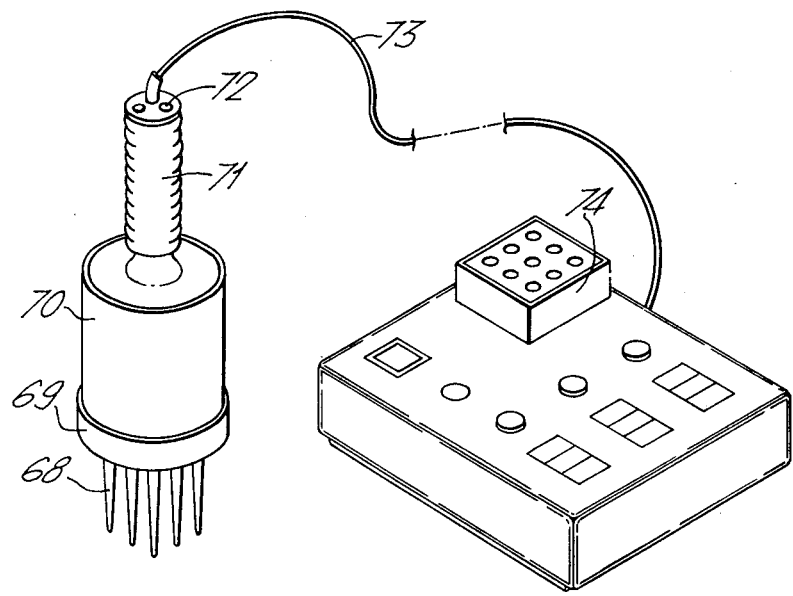
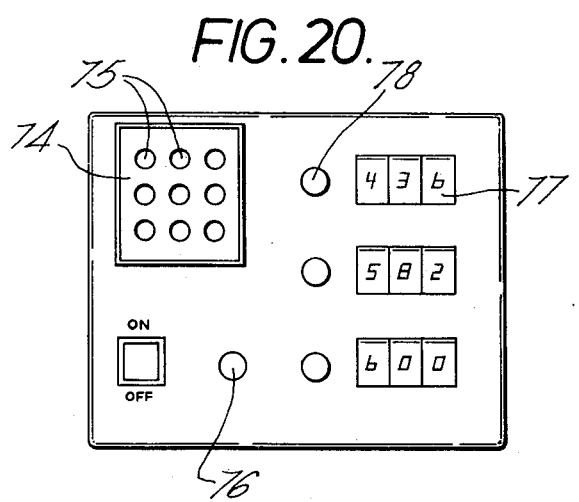

APPARATUS FOR ACCURATE PIPETTING OF SMALL LIQUID VOLUMES

This invention relates to a method and an apparatus for accurate pipetting of small liquid volumes for sample and reaction mixtures.

In laboratories, work routines for measuring for instance the reaction rate of a certain enzyme are quite common. Reaction mixtures for these measurings are prepared for instance so that 50 µl of solution, containing the enzyme, is added to a test tube or cuvette which is thermoregulated at +37° C. After the temperature has settled to +37° C, one or several reagents at +37° C, usually containing a buffer, a substrate and a cofactor, are added.

The reaction rate of enzyme reactions depends greatly on the temperature of the reaction mixture. So it is very important that the temperature of the reaction mixture does not change because of pipettings. Bergmeyer (Z. Klin. Chem. Klin. Biochem. 11. Jg 1973, pp. 39 .... 45) has stated that the temperature in enzyme reaction measurements must not change, and the higher the temperature where the reactions are measured, the more difficult it is to keep the temperature constant. Bergmeyer has further noted that if the temperature of the reaction mixture significantly differs from the room temperature when pipetting liquids, the calibratings of pipettes do not hold, adding of liquids and shaking of reaction containers causes errors. It has been stated, however, that reaction rates of enzyme reactions should be measured at +37° C instead of +25° C or +30° C, and the incubators should operate at an accuracy of ±0.2° C (Scan. J. Clin. Lab. Invest. 33, 287 ... 306, 1974).

Usually the reagent is transferred by means of a manual pipette which also contains a pump and container section. Besides manual pipettes, also mechanical pipettes are used. These pipettes are kept freely on the laboratory table, or on a stand, so that the temperature of the whole pipette is very close to the room temperature.

Table I

| Time (sec.) | Temperature (° C) | | | | |
|---|---|---|---|---|---|
| | 200 µl | | | 400 µl | |
| | Mean | ± SD | | Mean | ± SD |
| 0–1 | 36,4 | 0,3(4) | 36,6 | 0,1(3) | |
| 5 | 34,0 | | 0,3 | 35,2 | 0,4 |
| 10 | 33,4 | | 0,4 | 34,4 | 0,4 |
| 15 | 32,9 | | 0,6 | 34,1 | 0,4 |
| 20 | 32,4 | | 0,5 | 33,8 | 0,3 |

Table I shows the temperature change of the water in the point container of a pipette as the function of the time when a pipette at the room temperature has been used for pipetting of distilled water thermoregulated at 37.1° C.

Pipettings have been carried out by means of a FINNPIPETTE 13 pipette which is adjustable for different volumes at a range from 200 to 1000 µl, and a FINNTIP 61 point container has been used.

The temperature of the distilled water drawn to the point container has been measured by means of a calibrated NTC resistance (a resistance with a diameter of 0.3 mm at the loop of a thin wire) connected to a digital voltage meter.

The temperature of the water to be pipetted was +37.1° C before the pipetting. The room temperature was +23.5° C.

From table I it can be seen that if 200 µl of distilled water at +37.1° C is pipetted by means of a manual pipette, the temperature of a water volume of 200 µl in the point container of the pipette at the room temperature has fallen from +37.1° C to +34.0° C, that is by 3.1° C, in 5 seconds. Correspondingly, the temperature of a water volume of 400 µl in the liquid container of a pipette at the room temperature has fallen by 1.9° C in 5 seconds. Usually, in fast pipetting, the pipetting time is the said 5 seconds. As the temperature of the liquid in the container of the pipette has fallen within this time, and this cooled reagent is transferred to a thermoregulated test tube or cuvette, it always takes a while until the original temperature has been reached in the test tube or cuvette.

Table II

| Time (sec.) | Temperature (° C) |
|---|---|
| −5 | 37,1 |
| 0–1 | 34,3 |
| 5 | 34,6 |
| 20 | 35,7 |
| 60 | 36,5 |
| 90 | 36,7 |
| 120 | 37,1 |

Table II shows the temperature change as the function of the time when a pipette at the room temperature has been used for pipetting 200 µl of thermoregulated liquid into 50 µl of liquid in a thermoregulated reaction container.

The temperature measurement has been carried out by means of a NTC resistance submerged in the reaction container and connected to a digital voltage meter.

The room temperature was +23.5° C.

From table II it can be seen that when pipetting 200 µl of water (+37.1° C) by means of a pipette at the room temperature so that the water is kept 5 seconds in the liquid container of the pipette and then at the moment 0–1 seconds moved to the reaction container which together with its contents (50 µl of water) has been regulated to +37.1° C, the temperature of the water mixture (50 + 250 µl of water) first fell down to 34.3° C. Only after 120 seconds the temperature settled back to the original 37.1° C.

Table III

| The time the distilled water has been at the point container of the pipette | The temperature of the liquid in the point container of a Thermoregulated pipette (° C) | | |
|---|---|---|---|
| Sec. | 200 µl | | 400 µl |
| | Mean ± SD | | |
| 0–1 | 37,03 | 0,03(3) | 37,05(1) |
| 5 | 36,90 | 0,10 | 37,00 |
| 10 | 36,66 | 0,11 | 36,80 |
| 15 | 36,43 | 0.05 | 36,50 |
| 20 | 36,20 | (1) | |

Table III shows the temperature change as the function of the time when a thermoregulated pipette is used. Pipettings and temperature measurements have been carried out as in connection with table I.

The point container of the pipette was thermoregulated at 37.05° C. The temperature of the water to be pipetted was 37.05° C. The room temperature was 23.5° C.

From table III it can be seen that if the point container of the pipette is thermoregulated at the temperature of the liquids to be pipetted, the temperature of a liquid volume of 200 μl fell only from 37.05° C to 36.9° C in 5 seconds, and correspondingly the reduction was even less with 400 μl. On the basis of this test, it is obvious that if a thermoregulated pipette is used, the temperatures of the reagents or the samples are maintained.

It is also obvious that by present pipetting methods, in which the liquids are transferred to containers at the room temperature or the liquids to be portioned are moved through portioning devices or pipes at the room temperature, it is not possible to control the temperatures of the liquids to be pipetted. From this it follows that the temperatures of reaction mixtures significantly different from the room temperature are changed during pipettings. When measuring the initial rates of enzyme reactions, the error in the temperature causes a great error in the final result. Also the settling of the temperature takes a long time.

The inventions relates to a method by means of which the accuracy in pipetting can be significantly improved. The method takes into consideration maintaining of the temperature, and when necessary, the volume of the liquid, as accurately as possible at the desired values when pipetting.

The method according to the invention is mainly characterized in that one or several pipettes with one or several point and/or multistep multiple pipettes are partly or completely fitted in a thermoregulated space in one single pipetting-incubating station or unit in such a way that at least the liquid containers of the pipette or pipettes are in the thermoregulated space, and that sample, reagent or reaction mixture test tubes or cuvettes, basins or test tube elements are contained in or formed as removable block members, thermoregulated at the same temperature, and when necessary, also a shaker and/or a storage section or container for components are also fitted in the said pipetting-incubating station and thermoregulated at the same temperature, so that the pipetting, shaking, storing, etc. of the samples and reaction mixtures is carried out in a centralized way within one single pipetting-incubating station in conditions thermoregulated in an exact predetermined way.

The invention relates also to an apparatus for carrying out the said method. The characteristics of the apparatus are set forth in claim 2.

Figure 2:
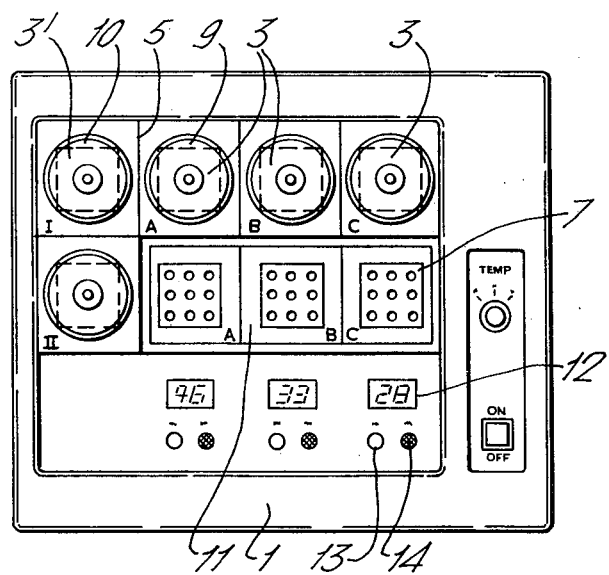
Figure 1A:
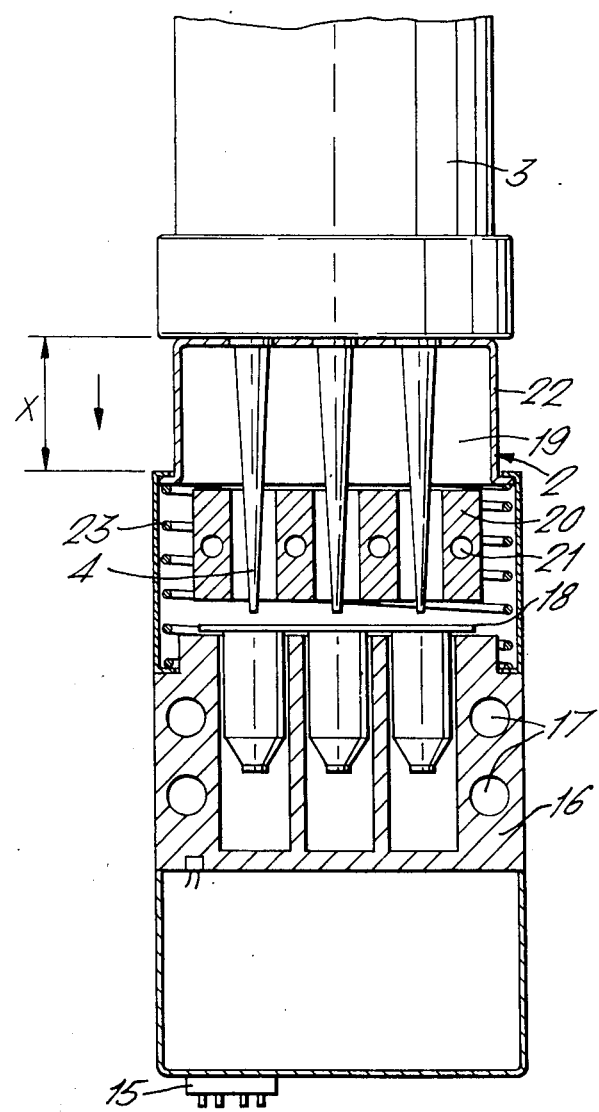
Figure 1B:
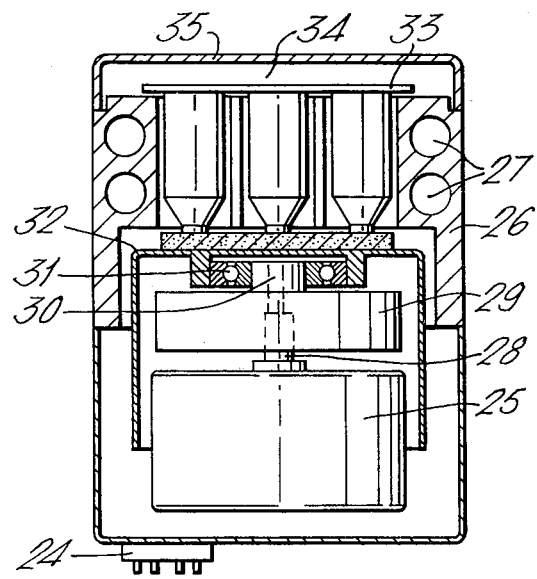
Figure 1C:
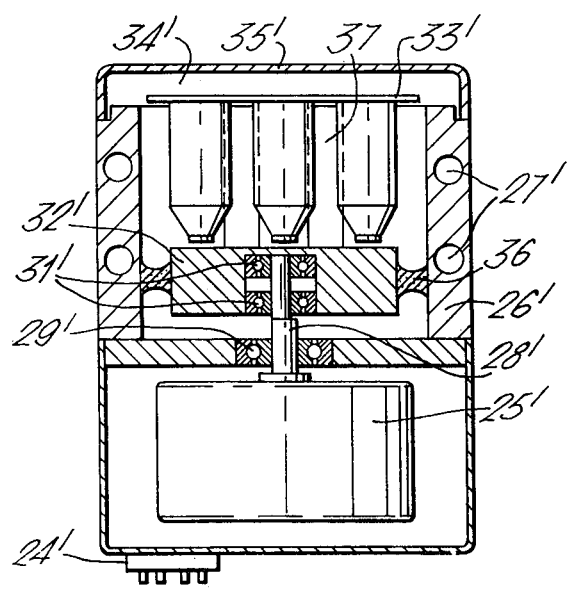
Figure 5:
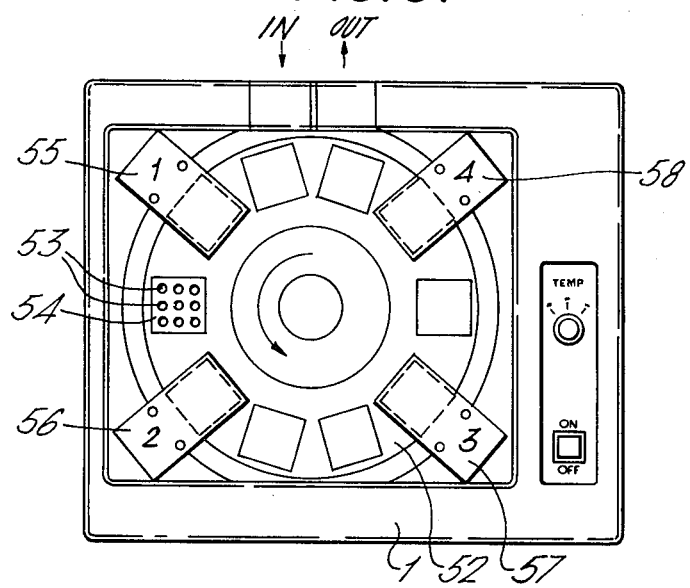
Figure 6:
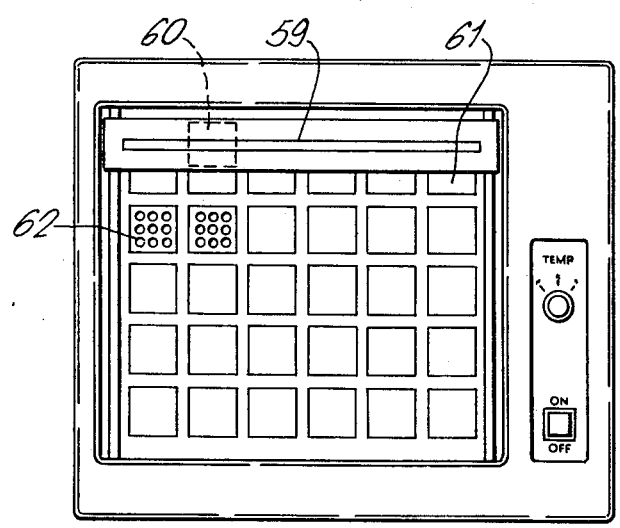
Figure 7:
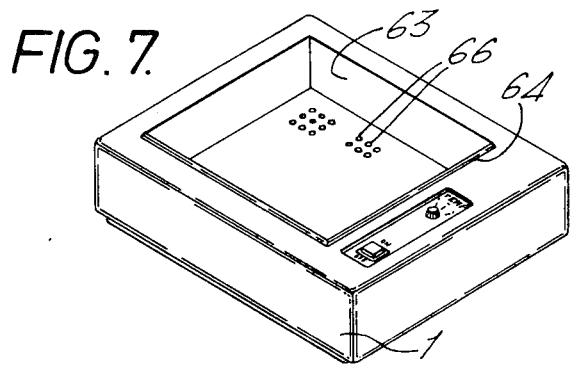
Figure 8:
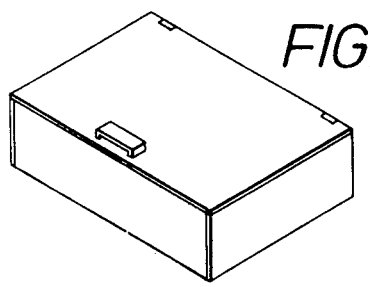
Figure 21:
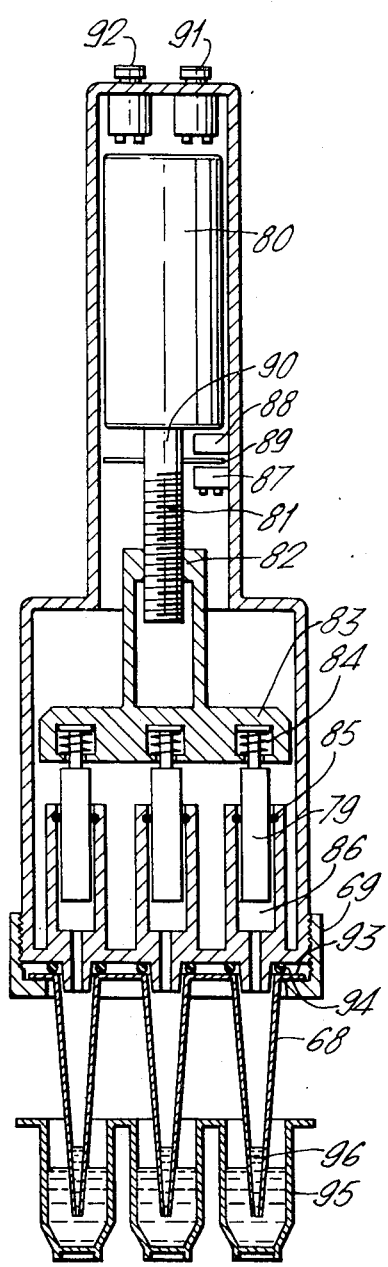
Figure 22:
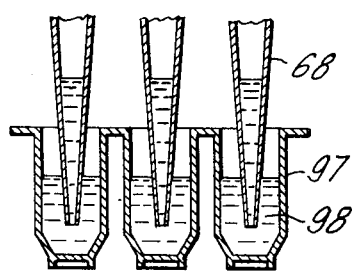
Figure 23:
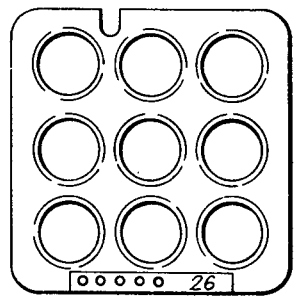

The invention is further illustrated in detail in the following with reference to the accompanying drawings, in which:

FIG. 1 shows schematically a perspective view of a pipetting-incubating station according to the invention, FIG. 1A shows a detail of the pipetting-incubating station of FIG. 1, in section taken at a pipette stand, FIGS. 1B and 1C show alternative shaker embodiments for the incubating station of FIG. 1, FIG. 2 shows a top view of the pipetting-incubating station of FIG. 1, FIGS. 3-6 show alternative embodiments of an incubating station, FIG. 7 shows a basic frame of a pipetting-incubating station, FIGS. 8-17 show separate elements to be fitted inside the basic frame of FIG. 7, FIGS. 18-20 show a multistep multiple pipette with a thermoregulated control unit, FIG. 21 shows a side view of a cuvette element and a multistep multiple pipette, in section, FIG. 22 shows the cuvette element and the points of the multiple pipette of FIG. 21 when the liquid containers of the multiple pipette are filled, and FIG. 23 shows a top view of a reagent block.

FIGS. 1 and 2 show a pipetting-incubating station assembled in a basic frame 1. Multiple pipettes 3 and 3' are supported by transparent pipette stands 2 sometimes referred to as cover means also referred to as cover means. The liquid containers 4 and 4' of the multiple pipettes 3 and 3' are inside the thermoregulated space 5 of the pipette stands 2. Reagent or sample basins 6 and 6', either fixed or loose, sometimes referred to as movable block members, referred to as movable block members, submerged in the basic frame, are in the same inner spaces 5. The liquid containers 4 and 4' of the multiple pipettes 3 and 3' with nine containers can be submerged to a certain depth into the basins 6 and 6', by pressing the multiple pipette against a spring force, for instance, and desired liquid volumes can be drawn into the liquid containers 4 and 4'. Instead of the reagent of sample basins 6 and 6', there can also be test tube elements each with nine test tubes, from which samples can be drawn into the corresponding liquid containers of the multiple pipettes. Also single test tubes can be used instead of reagent basins or test tube elements. The pipette stands 2 are provided with resistances around the reagent basins 6 and 6', similarly a resistance controls the temperature of the inner space 5. So the points 4 and 4' of the multiple pipettes 3 and 3' will be thermoregulated to the same temperature as the liquid in the reagent basins 6 and 6'. Also the surroundings of test tube elements 7 in shakers are thermoregulated. When pipetting with the thermoregulated pipettes from the reagent basins 6 to the test tube elements 7, the temperature of the liquids does not change. Liquid containers of pipettes, reagent basins, reagents, samples, test tubes or test tube elements, for instance, can be stored in a container 8, located in the basic frame 1 and provided with a lid.

FIG. 1A shows in detail the pipette stand 2 of FIG. 2. The pipette stand of FIG. 1A is connected to the basic frame by means of a connector 15, through which the pipette stand gets electric current and electric control from the basic frame. Electric resistances 17 are arranged at the frame 16 of the pipette stand and they thermoregulate a test tube element 18 or some other sample or reagent basin. Resistances 21 in a frame 20 thermoregulate the inner space 19 in the pipette stand 2. A multiple pipette 3 rests supported by a support 22 of the pipette stand, and the liquid containers 4 of the multiple pipette 3 can be submerged into the tubes of the test tube elements 18, a desired distance to a certain depth so that desired liquid volumes can be drawn into the liquid containers 4 of the multiple pipette. A spring 23 returns the support 22 of the multiple pipette to the upper position.

FIGS. 1B and 1C show two embodiments of a shaker, by way of examples. The shaker of FIG. 1B is connected to the basic frame by means of a connector 24 through which the shaker is electrically controlled and receives electric current for a motor 25 and resistances 27 in a frame 26.

A flywheel 29 is mounted on the shaft 28 of the motor 25. The shaft 30 of the flywheel is eccentrically connected to a shaking plate 32 by means of a bearing 31. The eccentric movement of the shaking plate 32 shakes the liquid in the tubes of the test tube element 33. The test tube element is located in a thermoregulated space 34, and this space can be closed by means of a lid 35.

The shaker of FIG. 1C comprises a connector 24', a motor 25', a frame 26' and resistances 27' in the frame. The shaft 28' of the motor 25' is supported by a bearing 29'. An eccentric shaft 30' is an extension of the shaft 28' and is mounted on bearings 31'.

The eccentric movement of the shaft 30' is transferred by means of the bearings 31' to a shaking plate 32', which is attached to the basic frame 26' by means of resilient supports 36' so that the shaking plate 32' will not rotate. The shaking plate 32' is provided with supports 37 on which a test tube element 33' rests. A thermoregulated air space 34' can be covered by means of a lid 35'.

FIG. 2 shows a top view of a pipetting-incubating station. The figure shows multiple pipettes 3, one for each sample test tube element 9 (A, B, C). Corresponding multiple pipettes 3' are provided for pipetting reagents I and II from reagent basins 10.

Reaction mixture test tube elements 7 (A, B, C,) are in a thermoregulated unit 11 and can be covered by a lid, if necessary. The thermoregulated unit 11 can be either fixed or loose in the basic frame 1. Instead of the unit 11, there can be a shaking unit which shakes the contents of each test tube element 7 after pipetting.

One or several separate test tubes can also be fitted into the shaker. The shaker can also be located somewhere else in the basic frame 1. A multiple pipette 3 is provided for each sample element 9 and so there is a liquid container 4 of the multiple pipette 3 for each of the nine samples in a test tube element 9. In this way contamination is avoided.

Samples are transferred by means of the multiple pipettes 3 to the corresponding reaction mixture test tube elements 7 (A, B, C). After this, incubation medium reagent I, for instance, can be pipetted into each test tube element 7 (A, B, C) from the reagent basin 10 by means of a corresponding multiple pipette 3'. The reagent basins 10 can be preincubated for a desired time. The time can be set by means of finger switches 12, for instance. The control unit can include also a starting time switch 13 and an alarm light or a signal lamp 14. After this, starting reagent II is pipetted by means of a corresponding multiple pipette first to a reagent test tube element 7A, for instance, and after a certain time, the reaction mixtures in this test tube element are transferred to metering, for instance. The temperatures of the liquids pipetted do not change in the pipetting-incubating station during the pipetting. The shaker completes the station so that after each pipetting, shaking can be done in a thermoregulated shaker. In this way it is not necessary to transfer test tubes or test tube elements to another apparatus for shaking which would cause a temperature change and at the same time an error in the reaction results.

Alternative embodiments to the above pipetting-incubating station are described in the following.

Figure 3:
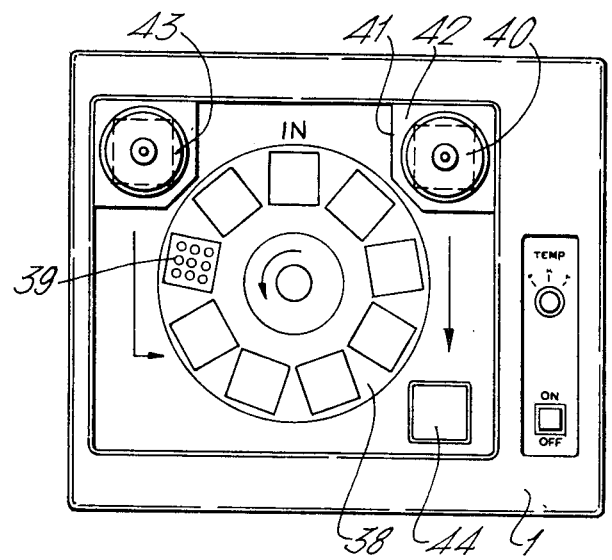

The apparatus of FIG. 3 has a thermoregulated disk 38 in the basic frame 1. The disk rotates at a rate defined by a timing unit and has test tube elements or test tube groups 39 in it. The apparatus includes multiple pipettes 40 fitting into these test tube elements of the groups. The multiple pipettes are in a thermoregulated pipette stand 41. The inner space 42 of the pipette stand contains the point containers of the multiple pipettes 40 and a sample or reagent basin 43 submerged in the basic frame 1. The basic frame contains also a shaker 44, fixed or detachable. The disk 38 can be detachable, and if necessary, separately thermoregulated, and it can also be covered by a suitable lid so that heat is prevented from escaping.

Figure 4:
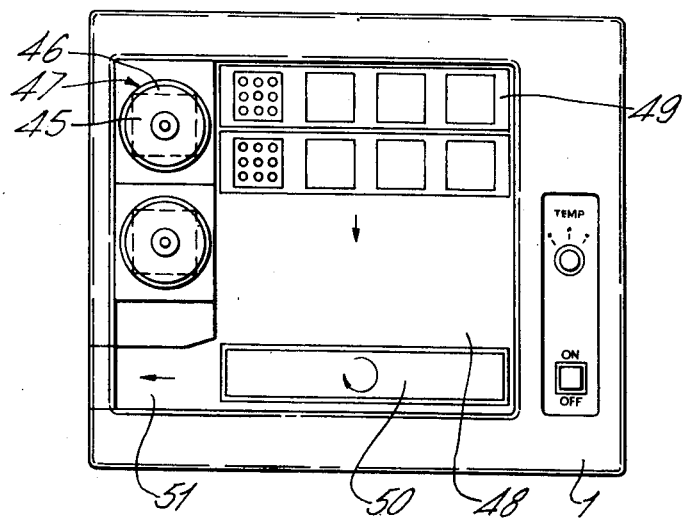

FIG. 4 shows an assembled apparatus with two units 47, each formed by a multiple pipette 45 and a sample test tube element or reagent basin, assembled in a basic frame 1. A test tube element or test tube stands 49 are thermoregulated on the heat plate 48 of the apparatus. From the heat plate 48 the stand 49 can be transferred to a shaker 50 from where a thermoregulated line 51 leads to a metering device.

FIG. 5 shows an apparatus having a disk 52 in a basic frame 1. Sample cuvettes 53 are in groups 54 in the thermoregulated space of the disk 52, and reagent portioning devices 55 and 56 are grouped in a way corresponding to the sample cuvettes. The apparatus can include one or several reagent portioning devices or shakers 57 in a suitable order and at a suitable distance from each other. The apparatus can also include a metering device 58 for metering the absorbance of the solutions. All the said devices are in one common or several separate thermoregulated spaces. The apparatus can operate completely or partly automatically, or the various transfers and pipettings can be done manually. The metering device can be a meter measuring one or several samples at the same time, or it can be one- or multi-channelled.

FIG. 6 shows an apparatus where the pipetting or portioning unit 60 of the automatic portioning device 59 automatically moves to a desired sample or reagent basin 61 or a test tube element 62. The whole apparatus or its sections separately can be thermoregulated.

FIG. 7 shows a basic frame 1. The inside 63 of this basic frame can be furnished with different elements depending on the purpose it is used for. The opening of the inside 63 of the basic frame can be covered by a transparent lid 64.

Figure 13:
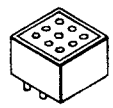
Figure 9:
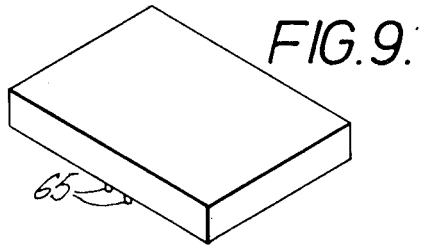
Figure 14:
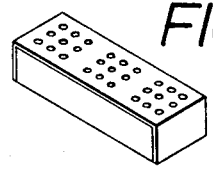
Figure 10:
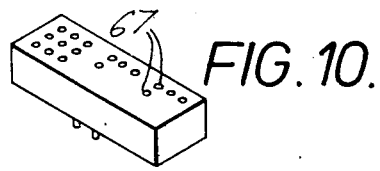
Figure 15:
Figure 11:
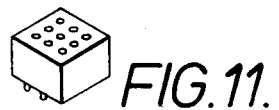
Figure 16:
Figure 12:
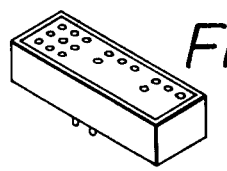
Figure 17:
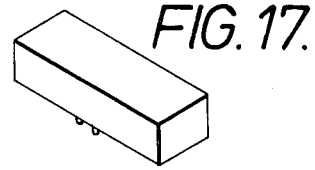

A heat plate of FIG. 9 can be fitted on the bottom of the inside 63 of the basic frame 1. The heat plate is provided with a connector 65 fitting into the connectors 66 on the bottom of the basic frame. The heat plate and all the other elements receive electric current and the necessary controlling from the basic frame 1 through the connectors. A heat box of FIG. 8 can be fitted in the inside 63 of the basic frame. FIG. 10 shows a thermoelement for three test tube elements. This thermoelement can be provided with openings 67 for tubes of various sizes. FIG. 11 shows a thermoelement for one cuvette element. FIG. 12 shows a shaker for three cuvette elements which shaker can be connected to the basic frame 1. FIG. 13 shows a shaker for one cuvette element. FIG. 14 shows a thermostand for three multiple pipettes which stand can be connected to the basic frame 1 or stand freely on a table. FIG. 15 shows a thermoelement for one multiple pipette, and FIG. 16 shows a thermoelement for a reagent basin. FIG. 17 shows a control unit for various operations (time, temperature, alarm, shaking, automatic control, etc.). The elements shown in FIGS. 10–15 may all be referred to as removable block members. The elements shown in FIGS. 10–15 may all be referred to as removable block members.

When small liquid volumes are pipetted by means of pipettes available on the present market, a volume shown by a calibrated scale or a constant volume of liquid can be accurately drawn into adjustable or constant-volume pipettes. When the liquid container of such a pipette is emptied, some liquid always remains on the inner surface of the liquid container of the pipette, either as a thin film or as vague droplets. Robert E.

Wenk with this fellow workers (Clinical Chemistry 20/3, 320 . . . 323, 1974) noted that a pipette at one setting gave different volumes in the pipetting, depending whether an unused or used liquid container was used. Further it was observed that the smaller the volume pipetted, the greater the error in percentage in pipetting. Heleen G. F. Zwart (Tijdschrift voor Medische Analisten 29/4, 127 . . 131, 1974) has reported that, depending on the manufacturer of the pipette, the calibrating of most pipettes included great calibrating errors.

In the pipettes in general use, pipetting one sample at the same time, the volume to be pipetted is defined by the length of the piston movement. Each pipette is always calibrated at the manufacturing stage in the factory to correspond to the volume shown by the pipette scale or given on the pipette. Most pipettes presently on the market thus do not always pipet the liquid volume shown, and further, the emtying of the points of the pipette is vague.

The purpose of a multistep multiple pipette is to first accurately take several liquid volumes (samples or reagents) in succession into the containers where the samples are partially mixed or they can be separated from each other by a small air column. When the multistep multiple pipette is emptied, each liquid volume, either partially mixed or in succession in each liquid container, is transferred to a cuvette corresponding to a liquid container of the multistep pipette.

FIG. 18 shows a multistep multiple pipette with liquid containers 68 which are joined to the body 70 by an instant joiner 69. A handle section 71 with operating buttons 72 is joined to the body 70. The handle section is connected to a control unit for a multistep multiple pipette, shown in FIG. 19, by an electric wire 73. A top view of the control unit is shown in FIG. 20. The control unit includes a stand 74 for a multistep multiple pipette. The pipette is set onto the stand so that the liquid containers 68 pass through the holes 75 of the stand into the inside of the stand. The inside of the stand is thermoregulated to a temperature required in each case. The temperature of the inside can be set by means of a control button 76. Finger switches 77 are used for setting the volumes of the samples and reagents to be pipetted. A signal light 78 indicates when a pipetting is completed.

The length of the stroke of the pistons 79 in a multistep multiple pipette is determined according to the number of rotations or parts of a rotation an electric motor 80 has moved a common mover 83 of the pistons by means of a fine-threaded rotating shaft 81 and a threaded tube 82 connected to the shaft. The common mover 83 of the pistons has the pistons mounted with a small sideways clearance and with no clearance at the longitudinal direction of the pistons or supported by a spring 84 in such a way that the friction directed to the pistons in an O-ring 85 cannot move the piston in the longitudinal direction of the piston. The O-ring 85 seals the connection between the cylinder space 86 and the piston 79. Rotations or parts of a rotation are counted by a light diode 87. The light diode 87 receives broken light from a light source 88. The light is broken by a groove plate 89 which is mounted at the connection of the shaft 90 of the motor 80 and the threaded shaft 81. This groove plate 89 breaks the light coming from the light source 88 to the light diode 87 either once or several times as the threaded shaft 81 rotates one rotation. From these broken signals the electronics in a setting unit of FIGS. 19 and 20 count such a number that corresponds to volumes set at the setting elements 77 of the setting unit. Instead of the above, a multiple pipette may be provided with an electric step motor with suitable controlling electronics. The setting unit is also provided with a stand 74 for a multistep multiple pipette and the multistep multiple pipette is connected to its setting unit by a cable 73. The activating impuses for the multistep multiple pipette can be given by switches 91 and 92 in the multistep multiple pipette or switches 78 in the setting unit. All the electronics and the programming sections of the multistep multiple pipette can also be included in the multistep multiple pipette structure itself. The point plates 93 of the multistep multiple pipette are attached by means of an instant joiner screw 69 described in the multiple pipette inventon (Finnish Pat. No. 47460), in such a way that each liquid container 68 of the point plate comes to an air tight connection with the corresponding cylinder space 86 by means of a seal 94. The multistep multiple pipette can have a varying number of point containers.

The multistep multiple pipette can be electrically programmed to move at the filling or emptying stage of the multiple pipette either one or several distances of a certain length, corresponding to certain liquid volumes. Such an electronic multichannel multiple pipette does not present any calibrating problems and its mechanical moving parts move more accurately than manually operated pipettes.

The functioning of a multistep multiple pipette is described in the following as an embodiment in connection with preparing an enzyme reaction: The multistep multiple pipette is programmed to draw samples of 30 $\mu$l into each of the nine liquid containers 68 from a cuvette element 95. After this, the multipstep multiple pipette is moved to a cuvette element 97 (FIG. 23) where reagents 98 have been measured, and the pipette is given an order to continue the drawing operation for 270 $\mu$l more. Each liquid container 68 of the multistep multiple pipette now contains 300 $\mu$l of liquid. When the multistep multiple pipette receives an emptying order, the partially mixed sample and reagent in the liquid container of the device are transferred to cuvettes of the element 95. At the emptying stage the multistep multiple pipette also received an order to move a distance somewhat longer than the movement or movements by which the device was filled, and after that to return to the filling position. This ensures that the liquid containers are emptied completely. When the sample and reagent have been drawn in succession into the containers of the multistep multiple pipette in the way described above, small sample volumes together with reagent are discharged very accurately from the containers of the multistep multiple pipette to the cuvettes of the cuvette element. Also an order other than the above can be used in pipetting the sample, reagent or reagents. Further, the multistep multiple pipette can be programmed to draw a large volume of liquid into each liquid container, and this volume can be programmed to be emptied in several smaller volumes. In this way small liquid volumes can be portioned very accurately.

A multistep multiple pipette described above or a liquid portioning device of some other type can, of course, be thermoregulated, either at the liquid containers or completely. A multistep multiple pipette or some other pipette can be programmed to automatically transfer liquids from one or several certain positions to one or several certain positions. Besides the liquid containers of a multistep multiple pipette or some other liquid portioning device being thermoregulated, the whole apparatus can be in a completely or partly thermoregulated space.

The invention is not restricted to the above embodiments. It can vary considerably within the scope of the claims.

I claim:

1. Apparatus for pipetting liquid volumes including a frame having wall means which form an enclosure, a plurality of removable block members located in said enclosure, each said block member having means therein to hold a plurality of liquid containing means, a plurality of liquid containing means located respectively in at least some of said holding means, a plurality of cover means covering said plurality of removable block members, means for thermoregulating said enclosure to maintain the same and said block members contained therein at substantially the same temperature, a pipette having a plurality of liquid containers, a plurality of opening means in each said cover means, said plurality of opening means receiving said plurality of liquid containers of said pipette and locating said plurality of liquid containers in said enclosure above one of the plurality of liquid containing means, means movably mounting each of said cover means whereby said cover means may be moved toward and away from said removable block members, movement of one of said cover means toward a removable block member with said plurality of liquid containers received in said plurality of opening means in said cover means causing said plurality of liquid containers to move into the plurality of liquid containing means to remove liquid which may be transferred to another of said plurality of liquid containing means by inserting said plurality of liquid containers through said plurality of opening means in another said cover means.

2. Apparatus for pipetting liquid volumes including a frame having wall means which form an enclosure, cover means for covering said enclosure, liquid containing means located within said enclosure, means for thermoregulating said enclosure to maintain the same at a desired temperature, a pipette having at least one liquid container, at least one opening means in said cover means, said at least one opening means receiving said at least one liquid container of said pipette and locating said at least one liquid container in said enclosure above said liquid containing means, said liquid containing means comprising a removable block member having a heating element and a test tube receiving opening, a test tube in said test tube receiving opening, said cover means located above said test tube and being vertically movable between upper and lower positions and having spring means biasing said cover means to said upper position, exertion of a downward force on said cover means causing said liquid container of said pipette to move into said test tube.

3. Apparatus as claimed in claim 2, wherein a shaker is disposed in said thermoregulated enclosure for the purpose of shaking said liquid containing means.

4. Apparatus as claimed in claim 2, wherein said pipette has a plurality of liquid containers which are received in a corresponding plurality of opening means in said cover means.

5. Apparatus as claimed in claim 2, wherein a plurality of liquid containing means each comprising a removable block member are provided in said enclosure with a plurality of cover means respectively located above said plurality of liquid containing means, each cover means has at least one opening, a plurality of pipettes are provided each having at least one liquid container each received in an opening means in a respective cover means.

6. Apparatus as claimed in claim 2, wherein said frame and said removable block member have engageable electrical contact means to supply electrical power to said heating element.

* * * * *